United States Patent
Onishi et al.

(10) Patent No.: US 6,458,111 B1
(45) Date of Patent: Oct. 1, 2002

(54) DISPOSABLE ABSORBENT ARTICLE

(75) Inventors: Kazuaki Onishi; Norihiko Ishikawa; Yoko Yabe, all of Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/577,142

(22) Filed: May 24, 2000

(30) Foreign Application Priority Data

May 31, 1999 (JP) ............................................. 11-152898

(51) Int. Cl.[7] ................................................. A61F 13/15
(52) U.S. Cl. .................. 604/385.01; 604/369; 604/378; 604/381
(58) Field of Search ............................... 604/385.1, 369, 604/378, 381, 385.19, 385.24, 398, 380, 385.2, 387, 397–402, 385.01, 385.08, 385.101

(56) References Cited

U.S. PATENT DOCUMENTS

| | | | | |
|---|---|---|---|---|
| 4,421,511 A | * | 12/1983 | Steer et al. ................... 4/144.3 |
| 5,306,266 A | * | 4/1994 | Freeland ...................... 604/358 |
| 5,417,680 A | * | 5/1995 | Kimura et al. ............... 604/358 |
| 5,462,541 A | * | 10/1995 | Bruemmer et al. ......... 604/378 |
| 5,520,674 A | * | 5/1996 | Lavon et al. ................ 604/369 |
| 5,624,422 A | * | 4/1997 | Allen .......................... 604/378 |
| 5,674,213 A | * | 10/1997 | Sauer .......................... 604/378 |
| 5,676,661 A | * | 10/1997 | Faulks et al. ........... 604/385.21 |
| 6,017,336 A | * | 1/2000 | Sauer .......................... 604/369 |
| 6,022,338 A | * | 2/2000 | Putzer ......................... 604/378 |
| 6,133,501 A | * | 10/2000 | Hallock et al. ............. 604/369 |

* cited by examiner

*Primary Examiner*—A. Vanatta
*Assistant Examiner*—Robert H. Muromoto, Jr.
(74) *Attorney, Agent, or Firm*—Lowe Hauptman Gilman & Berner, LLP

(57) ABSTRACT

A disposable absorbent article including a fecal matter retaining layer, the retaining layer including a three dimensional structure having a thickness of 5~100 mm adapted to be placed against a wearer's hip is formed with at least one opening having an area of 20~30000 mm$^2$ and at least one fecal matter retaining cavity having a depth of 2.5 mm.

29 Claims, 4 Drawing Sheets

DISPOSABLE ABSORBENT ARTICLE

BACKGROUND OF THE INVENTION

This invention relates to disposable absorbent articles such as disposable diapers, and more particularly, disposable diapers for disposal of fecal matter, particularly of loose passage.

Infants excrete fecal matter often in the form of loose passages and there have already been proposed various disposable diapers and absorbent articles suitable for disposal of such loose passages. For example, Japanese Patent Application Disclosure No. 1987-125001 describes a disposable diaper including a topsheet formed with many apertures each having a diameter of 2~8 mm, an absorbent pad and a fibrous cushion layer made of synthetic fiber having a fineness of 6~12 d and disposed between the topsheet and the absorbent pad.

The fibrous cushion layer has a thickness of 4~100 mm and a density of 0.005~0.18 $g/cm^3$. Loose passage moves through the apertures into the fibrous cushion layer and held therein without further moving in contact with a wearer's skin. In this manner, one of causes for eruption and/or uncomfortableness due to wearing the diaper.

Japanese Patent Application Disclosure No. 1987-276002 describes a surface structure of a disposable diaper in which a topsheet is formed with many apertures each having an area of 7~50 $mm^2$. The apertures are distributed at a pitch of 6~20 mm to have an open area ratio of 15~70% as a whole. A fibrous assembly layer underlying the topsheet is formed by component fibers heat-sealed together. This fibrous assembly layer has a thickness of 2~10 mm and a weight of 20~80 $g/m^2$. In its wetted condition, the layer exhibits an elastic recovery from its compressed volume by 50% or more. This diaper of prior art is claimed to offer the same effect as that of the previously described diaper of prior art.

Japanese Patent Application Disclosure No. 1997-299402 describes an absorbent article including a liquid-pervious top layer, a liquid-impervious back layer, a liquid-absorbent core disposed between these two layer and a liquid-filtering layer disposed between the top layer and the core. The top layer is formed alternately with ridges and troughs, wherein each of the troughs is formed with a plurality of apertures and ribs projecting from peripheral edges of the respective apertures toward the back layer. The liquid-filtering layer presents a thickness of 1.0 mm or more under a pressure of 30 $g/cm^2$ and has an average inter-fiber distance of 150 $\mu m$ or more. An effect offered by such absorbent article is similar to the effect of the previously described articles of prior art.

With the diaper and the absorbent article of prior art which have been described above, the fibrous cushion layer or the liquid-filtering layer underlies the top layer or the topsheet closely in contact with the lower surface thereof. Accordingly, the fibrous cushion layer or liquid-filtering layer likely chokes up the apertures of the top layer or topsheet. Loose passage can move into the fibrous cushion layer or liquid-filtering layer only in regions of such layer extending more or less into the respective apertures. While it will be possible for loose passage to move into the fibrous cushion layer or liquid-filtering layer even if each of the apertures has not adequately large open area, a rapid movement of loose passage can not be expected in this case. When it is tried to enlarge the open area of each aperture and thereby to accelerate the movement of loose passage, fibers of the fibrous cushion layer or the liquid-filtering layer extending into the respective apertures would discomfortably irritate a wearer's skin. Since the fibrous cushion layer or liquid-filtering layer often comprises fibers of a relatively high fineness, such irritation is correspondingly intense and enlargement of the open area would be necessarily limited.

SUMMARY OF THE INVENTION

It is an object of this invention to provide a disposable absorbent article giving a wearer a good feeling to wear it and allowing fecal matter, particularly loose passage to rapidly move downward from a topsheet.

According to a first aspect of this invention, there is provided a disposable absorbent article having an inner surface intended to come in contact with a wearer's skin and an outer surface opposed to the inner surface, the inner surface being provided with fecal matter retaining cavity or cavities adapted to receive fecal matter discharged on the inner surface so that the article is put on a wearer's body with a region including the fecal matter retaining cavity or cavities placed against a predetermined region of a wearer's hip extending around the anus, wherein: a fecal matter retaining layer having a thickness of 5~100 mm is formed with at least one said fecal matter retaining cavity comprising an opening having an area of 20~30000 $mm^2$ and a depth of at least 2.5 mm and the retaining layer comprises a three dimensional network structure having air/water permeability in a thickness direction thereof defined between the inner and outer surfaces and in a planar direction thereof intersecting the thickness direction thereof at right angles and elastic compressivity in the thickness direction.

According to a second aspect of this invention, there is provided a disposable absorbent article comprising a hydrophobic topsheet having an opening through which fecal matter can pass, a fecal matter retaining layer, a moisture absorbent layer and a liquid-impervious backsheet successively laminated one with another in this order, wherein: the topsheet is formed with at least one the opening having an area of 20~30000 $mm^2$; and the retaining layer is an elastic member having a thickness of 5~100 mm, air/water permeability in a thickness direction thereof and in a planar direction thereof intersecting the thickness direction at right angles, elastic recovery from a compressed state thereof of at least 50% in the thickness direction and a fecal matter retaining cavity formed immediately below the opening of the topsheet so as to have substantially the same open area as the area of the opening and a depth of at least 2.5 mm.

DETAILED DESCRIPTION OF THE PREFERRED EMBODIMENTS

Details of a disposable absorbent article according to this invention will be more fully understood from the description of a disposable diaper as one embodiment given hereunder with reference to the accompanying drawings.

Figure 1:
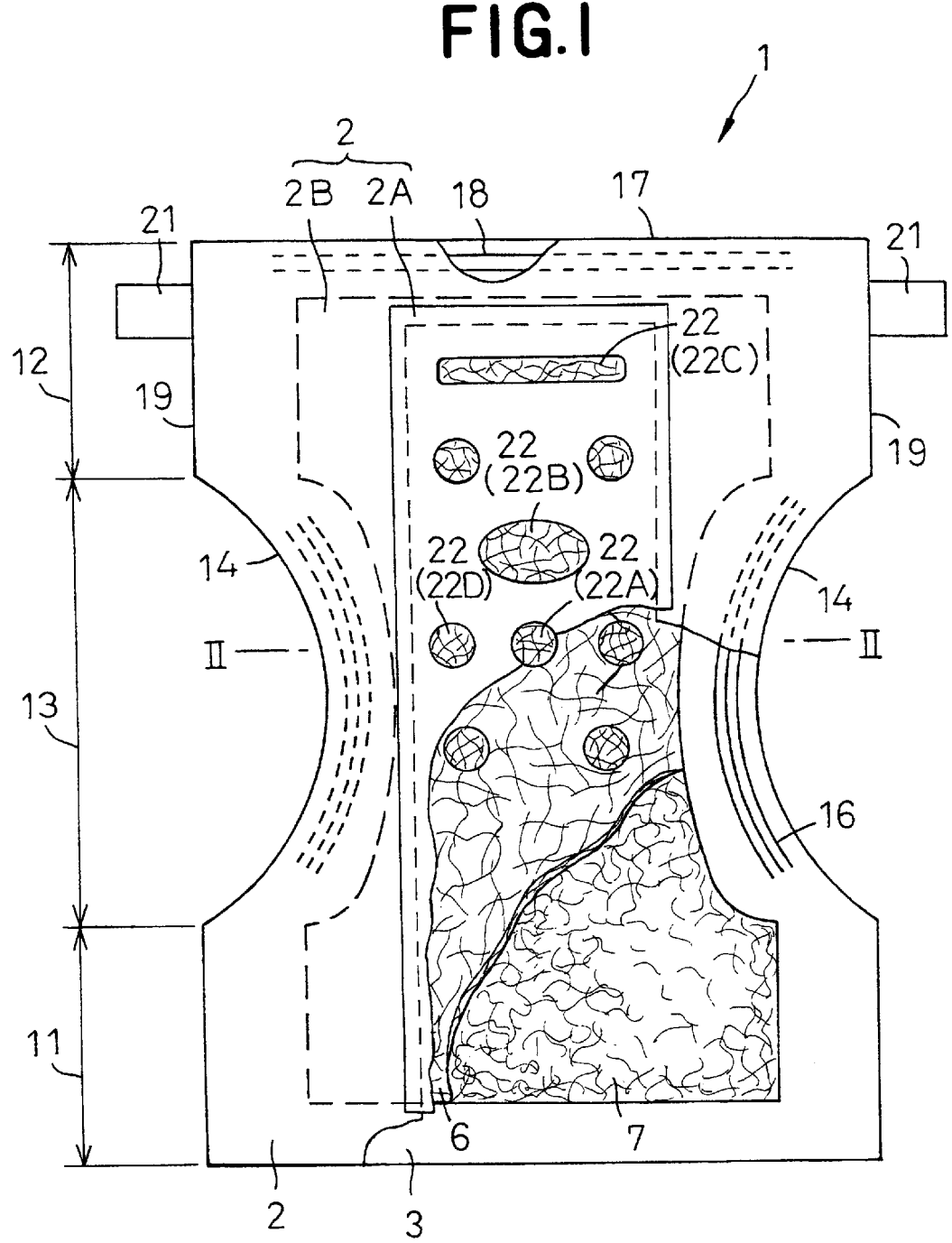
FIG. 1 is a partially cutaway plan view showing a disposable diaper constructed according to a principle of this invention.

A disposable diaper 1 shown by FIG. 1 in a partially cutaway plan view comprises a topsheet 2, a liquid-impervious backsheet 3, a fecal matter retaining layer 6 disposed between these two sheets 2, 3 and a moisture-absorbent layer 7 closely underlying the retaining layer 6. The topsheet 2 comprises a hydrophobic first sheet 2A lying in a transversely middle zone of the diaper 1 and a liquid-pervious second sheet 2B lying in a peripheral zone of the diaper 1. The retaining layer 6 and the absorbent layer 7 are substantially identical to each other in size as well as in shape. Specifically, they are hourglass-shaped. The topsheet 2 and the backsheet 3 are placed upon and joined to each other by means of hot melt adhesive agent (not shown) along their portions extending outward beyond peripheral edges of the retaining layer 6 and absorbent layer 7. The diaper 1 has longitudinally front and rear waist regions 11, 12 and a crotch region 13 extending between these two waist regions 11, 12. Transversely opposite side edges 14 of the crotch region 13 are curved inwardly of the diaper 1. The crotch region 13 is provided along the side edges 14 with elastic members 16 intended to be associated with respective leg-openings and the rear waist region 12 is provided along its longitudinal end 17 with an elastic member 18 intended to be associated with a waist-opening. The elastic members 16, 18 are disposed between the topsheet 2 and the backsheet 3 and secured under tension to the inner surface of at least one of these sheets 2, 3. A pair of tape fasteners 21 extend laterally from transversely opposite side edges 19 of the rear waist region 12.

The diaper 1 is formed on its inner surface with a plurality of fecal matter retaining cavities 22. The retaining cavities 22 are suitable particularly for retaining loose passage and have various plan shapes. While FIG. 1 shows the cavities of circular, oval and rectangular shapes 22A, 22B and 22C, the shapes of the cavities are not limited to them. However, it should be understood that the cavity 22B of a relatively large open area should be preferably formed in a zone of the diaper 1 intended to come in contact with a region of a wearer's body in the vicinity of anus.

Figure 2:
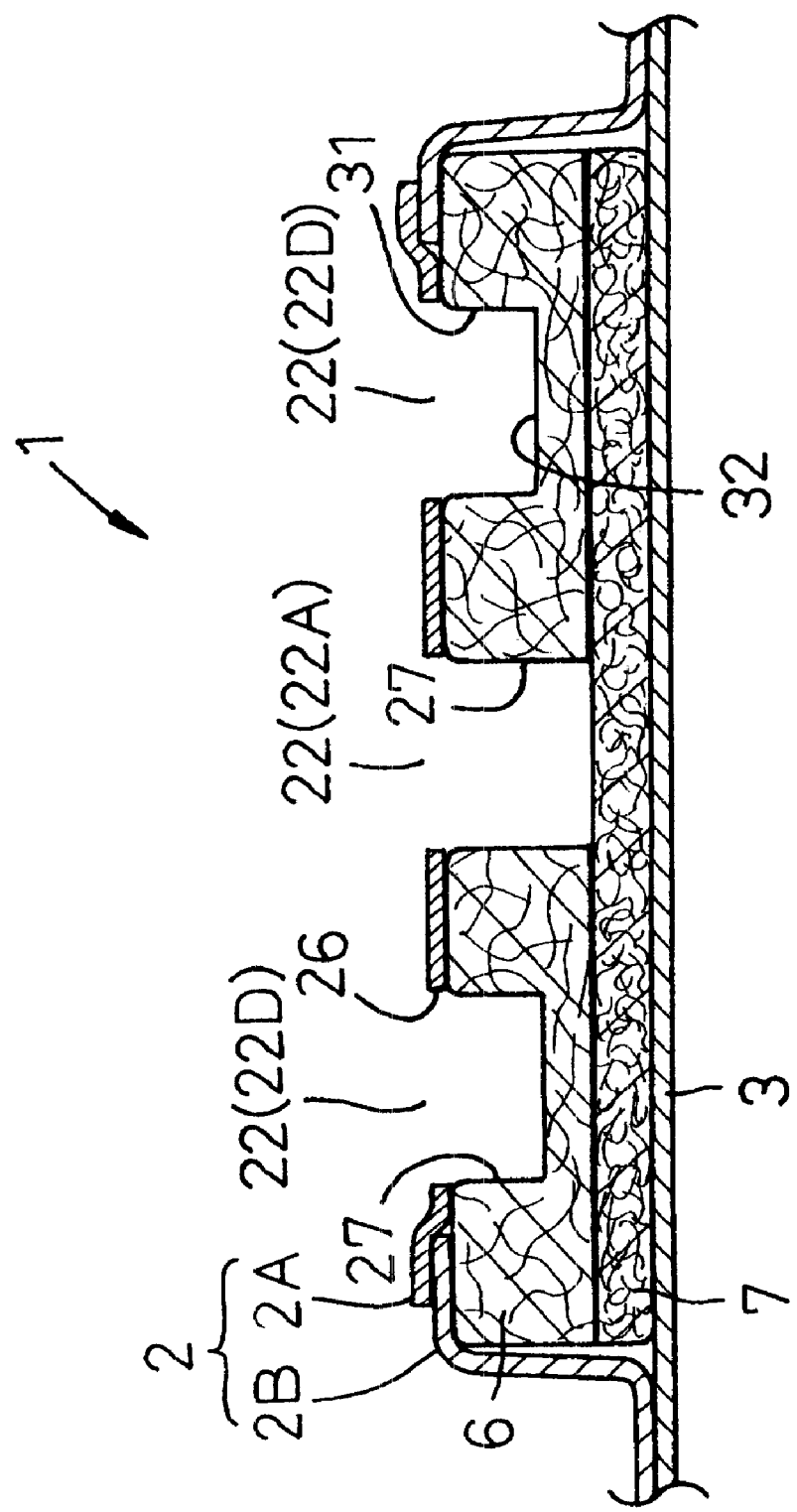
FIG. 2 is a sectional view taken along line II—II in FIG. 1.

FIG. 2 is a fragmentary sectional view taken along line II—II in FIG. 1. The first sheet 2A and the second sheet 2B constituting the topsheet 2 are placed upon and joined to each other by means of adhesive or heat-sealing technique. Such topsheet 2, the retaining layer 6 closely underlying the topsheet 2, the absorbent layer 7 closely underlying the retaining layer 6 and the backsheet 3 closely underlying the absorbent layer 7 are preferably joined together by means of adhesive or heat-sealing technique over their regions placed one upon another.

Each of the cavities 22 comprises an opening 26 formed through the topsheet 2 and a depression 27 formed on the retaining layer 6. The opening 26 is formed so as to occupy a region of the topsheet 2 in which the first sheet 2A overlies the retaining layer 6 and to have an open area of 20~30000 mm$^2$. The depression 27 is formed so as to underlie the opening 26 and has substantially the same open area as the open area of the opening 26. The depression 27 has a depth of at least 2.5 mm, preferably a depth corresponding to ½ or more of a thickness of the retaining layer 6 and more preferably a depth extending through the retaining layer 6. According to one embodiment illustrated, the cavity 22A has its depression 27 extending through the retaining layer 6 to the absorbent layer 7 and the cavity 22D has its depression 27 extending through approximately ½ or more of the thickness of the retaining layer 6. The number of the fecal matter retaining cavity 22 to be formed on the inner side of the diaper 1 may be single or plural. In the case of the diaper 1 formed with the single cavity 22, the cavity 22 of a relatively large open area may be formed in a region of the diaper 1 extending to cover wearer's anus. For example, the diaper 1 for infant may be formed with the single cavity 22 comprising the opening 26 having its open area of 3000~7000 mm$^2$ and the depression 27. In the case of the diaper 1 for adult wearer, the single cavity 22 should have its open area of 20000~30000 mm$^2$. Also when a plurality of the cavities 22 are provided, the cavities 22 should be formed principally in the region of the diaper 1 extending to cover a wearer's anus and the vicinity thereof. The first sheet 2A overlies the retaining layer 6 at least around the respective openings of the cavities 22.

The diaper 1 as has been described above may be realized by using stock materials as will be described. The first sheet 2A of the topsheet 2 may be preferably formed by a hydrophobic sheet such as a thermoplastic synthetic resin film or thermoplastic synthetic resin foamed sheet made of polyethylene or polypropylene or nonwoven fabric of thermoplastic synthetic fiber. The second sheet 2B may be formed by a hydrophilic or hydrophobic nonwoven fabric, porous plastic film. The topsheet 2 will have a thickness preferably of 0.01~0.3 mm so far as it is formed by a film or nonwoven fabric and preferably of 0.2~2 mm so far as its is formed by a foamed sheet.

The retaining layer 6 comprises elastics in the form of a three dimensional network structure having air/water permeability in a thickness direction between the topsheet 2 and the backsheet 3 as well as in a plane direction which is transverse to the thickness direction. Such retaining layer 6 may be formed by a thermoplastic synthetic fiber assembly such as a card web, bulky nonwoven fabric made of thermoplastic synthetic fiber or a foamed sheet such as a foamed urethane sheet having an open cell. When the thermoplastic synthetic fiber is used, it is preferred to use the crimped one. The retaining layer 6 has compressibility such that the layer 6 has a thickness $T_1$ of 5~100 mm under a load of 2 g/cm$^2$ for 5 min and preferably has a thickness $T_2$ corresponding to 40~80% of the thickness $T_1$ as it has been compressed under a load of 35 g/cm$^2$ for 5 min. The retaining layer 6 has an elastic recovery from its compressed state as will be described. Assumed that a load of 35 g/cm$^2$ is exerted upon the retaining layer 6 for 5 min, then this load is removed and the layer 6 is left for 30 min as it is before a load of 2 g/cm$^2$ is exerted again upon the layer 6 for 5 min, the layer 6 now elastically recovers a thickness $T_3$ corresponding to 50% or more of the thickness $T_1$. Along a peripheral surface 31 and a bottom surface 32 of the depression 27, the three dimensional structure comprising the fibrous assembly or the foamed sheet are exposed. It should be understood that the term "thickness" used herein means a thickness after a load of 2 g/cm$^2$ has been exerted upon the layer 6 for 5 min unless specified otherwise.

When the retaining layer 6 as has been described is formed by a nonwoven fabric of thermoplastic synthetic fiber, such nonwoven fabric preferably comprises the fiber having a fineness of 6~100 deniers at a basis weight of 100~1500 g/m$^2$. More preferably, 50% or more of total amount of fiber has a fineness of 10~70 deniers and component fibers are heat-sealed and/or mechanically entangled together so that the compressivity and elastic recovery from a compressed state, leaving a plurality of interstices providing desired air/water-permeability. While the retaining layer 6 is preferably formed by hydrophilic fiber, it is also possible to use hydrophobic fiber to form the retaining layer 6. The retaining layer 6 may be also formed by a mixture of thermoplastic synthetic fiber of 100 parts by weight and hydrophilic fiber of 1~100 parts by weight, the latter being not thermally meltable. Hydrophilic fiber suitable for such purpose may be selected from a group including natural fiber such as pulp fiber or cotton fiber, chemical fiber such as rayon fiber, synthetic fiber such as acrylic fiber and the other types of fiber such as polyvinyl alcoholic fiber and highly water absorbent resinous fiber.

The absorbent layer 7 comprises water absorbent fiber of highly water absorbent resin and is preferably able to absorb physiological saline at absorptivity of 8 g/g or higher. Additionally, the absorbent layer 7 preferably has a basis weight of 20~600 g/m$^2$ and a thickness $t_1$ of 0.1~20 mm and a density of 0.01~0.1 g/cm$^3$ under a load of 2 g/cm$^2$ for 5 min. Being compressed under a load of 35 g/cm$^2$ for 5 min, the absorbent layer 7 preferably has compressivity such that the layer 7 has a thickness $t_2$ corresponding to 40% or more of the thickness $t_1$. Assumed that a load of 35 g/cm$^2$ is exerted upon the layer 7 for 5 min, then this load is removed and the layer 7 is left as it is for 30 min before a load of 2 g/cm$^2$ is exerted upon the layer 7 for 5 min, the layer 7 preferably exhibits a resilent recovery from its compressed state such that the layer 7 recovers its thickness $t_3$ corresponding to 70% or more of the thickness $t_1$.

The water absorbent fiber as the material for this absorbent layer 7 may be selected from a group including natural fiber such as pulp fiber, chemical fiber such as rayon fiber and fibrous resin having a high water absorptivity. If desired, such fiber may be added with hydrophilic thermoplastic synthetic fiber or hydrophobic thermoplastic synthetic fiber treated to become hydrophilic. The water absorbent fiber preferably occupies 20~100% by weight of the absorbent layer 7. The thermoplastic synthetic fiber is preferably heat-meltable and has a fineness of 6~100 deniers. More preferably, the fiber having a fineness of 10~70 deniers occupies 50% by weight or more of the amount of thermoplastic synthetic fiber used to form the absorbent layer 7. The thermoplastic synthetic fiber is useful to form the absorbent layer 7 with the air/water permeable interstices and to improve a cushioning property of the layer 7. The resin of high water absorptivity useful to form the absorbent layer 7 is either fibrous or granular and an amount of this resin to be used is preferably in a range of 0~70% by weight of the absorbent layer 7. If desired, hydrophobic thermoplastic synthetic fiber of 20% by weight or less may be mixed into the absorbent layer 7 to improve a diffusion of water in the absorbent layer 7.

The backsheet 3 is formed by a thermoplastic synthetic resin film such as a polyethylene film having a thickness of 0.01~0.3 mm. This film may be either liquid-impervious or breathable liquid-impervious.

The disposable diaper 1 constructed as has been described above is advantageous in that fecal matter, particularly loose passage discharged thereon smoothly moves through the openings 26 of the topsheet 2 into the depressions 27 of the retaining layer 6. The retaining layer 6 comprises the three dimensional network structure allowing loose passage to move laterally and downward from the peripheral surface 31 and the bottom surface 32, respectively, and to promote such movement particularly when a wearer's body weight is exerted upon the retaining layer 6. An amount of loose passage having moved laterally from the depressions 27 is not concerned to come into contact with a wearer's skin since the retaining layer 6 is covered with the topsheet 2. So far as the retaining layer 6 has the compressivity and the resilent recovery from its compressed state as have already been described, it is not concerned that the retaining layer 6 might be extremely collapsed under a wearer's body weight without recovering a desired percentage of its initial thickness and an amount of loose passage might flow back outwardly of the depressions 27. The topsheet made of a hydrophobic nonwoven fabric or film offers an advantage that a wearer's skin can be protected from being soiled with loose passage over a large area since the topsheet 2 well resists exudation of loose passage therethrough and allows loose passage to flow into the cavities 22 before spreading over the topsheet 2. Moisture of loose passage is absorbed by the water absorbent materials contained in the retaining layer 6 and the absorbent layer 7 and consequently only the solid matter is left on the retaining layer 6. Fecal matter is no more in the state of loose passage and can not flow to soil a wearer's skin with fecal matter over a large area. There is no concern that the component fibers of the retaining layer 6 might project outwardly of the opening 26 and irritate a wearer's skin even if these component fibers are of a high fineness since the retaining layer 6 is formed immediately beneath the respective openings 26 of the topsheet 2 with the depressions 27.

Figure 3:
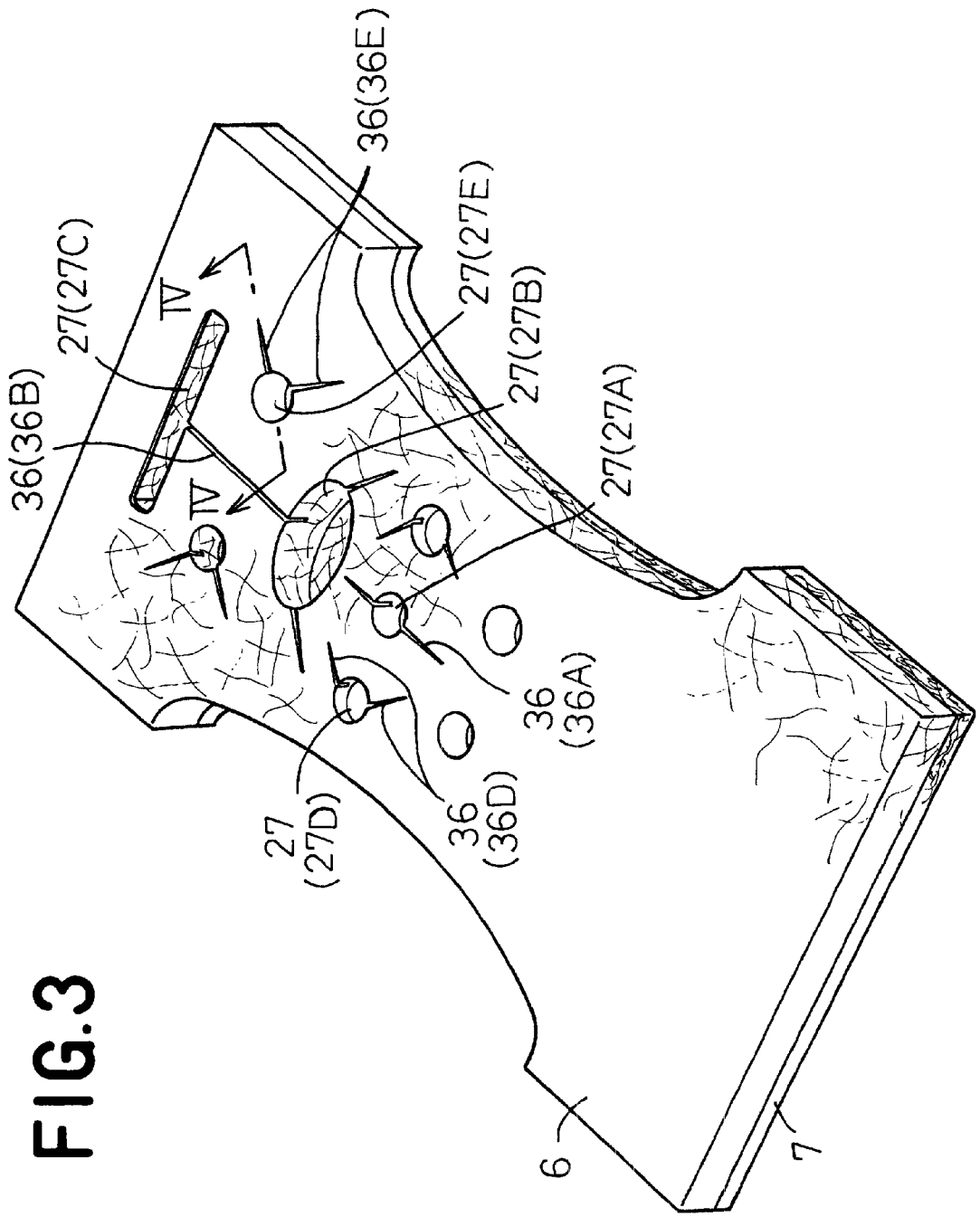
FIG. 3 is a perspective view showing a retaining layer according to the embodiment differing from that in FIG. 1.
Figure 4:
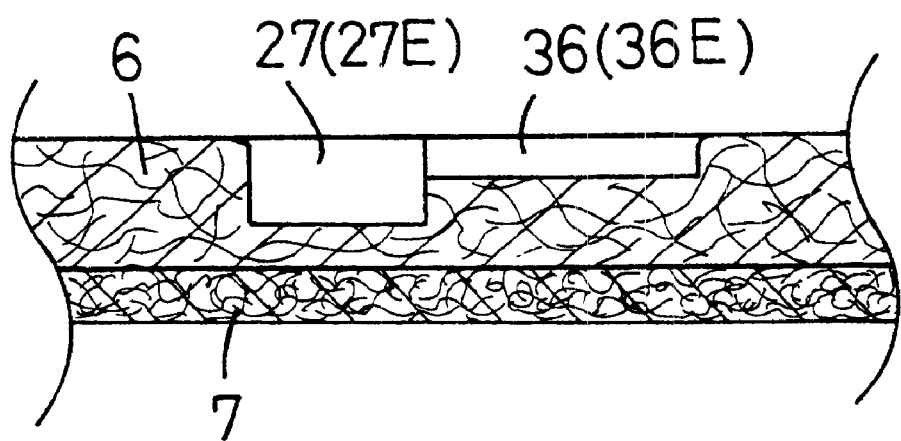
FIG. 4 is a fragmentary sectional view taken along line IV—IV in FIG. 3.

FIGS. 3 and 4 are respectively a perspective view and a fragmentary sectional view taken along line IV—IV in the perspective view showing another embodiment of the retaining layer 6 and the absorbent layer 7 adapted to be used in a article for disposal of fecal matter such as the diaper 1. In some of a plurality of the depressions 27 formed on the retaining layer 6, channels 36 extend from the depressions 27. For example, a channel 36B extends from the depression 27B to the depression 27C and channels 36A, 36D, 36E radially extend from the depressions 27A, 27D, 27E. Each of the channels 36 may have a cross-sectional area of at least 1 mm$^2$ and extend in a desired direction by a desired length. An amount of loose passage having flown into the respective depressions 27 of the retaining layer 6 can spread not only in a horizontal direction through the interstices of the three dimensional network structure but also through the channels 36 over a region of the retaining layer 6 as large as possible. A space of the retaining layer 6 may be efficiently used in this manner to substantially increase an amount of loose passage which can be retained in the diaper 1 without staining a wearer's skin therewith.

While the invention has been explained on the basis of one embodiment in the form of the disposable diaper 1, it is also possible to exploit this invention in the form of a pad exclusively for disposal of fecal matter adapted to be fastened to the inner side of a separate member such as a diaper, a diaper cover or shorts and then to be applied to a region of a wearer s body in the vicinity of anus. It is also possible to provide the retaining layer 6 or an assembly of the retaining layer 6 and absorbent layer 7 on the inner surface of the diaper 1 so as to cover only a portion thereof instead of providing them on the inner surface so as to cover it completely. Application of this invention is not limited to the diaper and the fecal matter disposal pad for baby but can be. adapted also as the similar articles for adult.

As will be apparent from the foregoing description, this invention proposes the article for disposal of fecal matter in which the topsheet is formed with the openings and the retaining layer underlying the topsheet is formed immediately below the openings with the depressions adapted to receive loose passage flowing thereinto. Such a unique arrangement is effective to prevent loose passage spreading over the topsheet and soiling a wearer's skin with loose passage over a large area. With the article of such an arrangement, in addition, it is not concerned that the component fibers of the retaining layer might project outwardly of the openings of the topsheet and irritate a wearer's skin.

According to one of the preferred embodiment of this invention, in which the retaining layer have the channels extending laterally from the respective depressions, it is possible to spread loose passage within the retaining layer in a relatively large range and thereby to increase an amount of loose passage which can be retained by the retaining layer without concern that a wearer s skin might be soiled with loose passage.

What is claimed is:

1. A disposable absorbent article having a crotch section corresponding to a crotch region of a wearer and front and rear sections disposed at longitudinally opposite ends of the crotch section, said absorbent article comprising an inner surface intended to come in contact with the wearer's skin and an outer surface opposed to said inner surface, said inner surface being provided with at least one fecal matter retaining cavity adapted to receive fecal matter discharged on said inner surface, said at least one fecal matter retaining cavity being arranged so that, when said article is put on the wearer's body, said at least one fecal matter retaining cavity will be placed against a predetermined region of the wearer's hip extending around his/her anus; wherein:

said absorbent article comprises a fecal matter retaining layer having a thickness of from about 5 to about 100 mm provided with said at least one fecal matter retaining cavity having an opening area of from about 20 to about 30000 mm$^2$ and a depth of at least 2.5 mm;

said retaining layer comprises a three dimensional network structure having air/water permeability in a thickness direction defined between said inner and outer surfaces and a planar direction intersecting said thickness direction at substantially the right angle and elastic compressivity in said thickness direction; and said retaining layer is present in all the front, crotch and rear sections of said absorbent article.

2. The article according to claim 1, wherein said inner surface of said article is formed at least partially by a top layer comprising a hydrophobic sheet, said top layer covering said retaining layer at least in the vicinity of said at least one retaining cavity, said at least one retaining cavity extending downward from an opening formed through said top layer to said retaining layer; and said outer surface of said article is formed by a back layer comprising a liquid impervious sheet.

3. The article according to claim 1, wherein said three dimensional network structure of said retaining layer is exposed through an inner peripheral surface of said at least one retaining cavity.

4. The article according to claim 1, wherein each of said at least one retaining cavity has a depth of at least ½ of a thickness of said retaining layer.

5. The article according to claim 1, wherein said at least one retaining cavity comprises a plurality of retaining cavities and at least one of said retaining cavities extends through said retaining layer.

6. The article according to claim 1, wherein said retaining layer elastically recovers at least 50% of an initial thickness thereof after being compressed in said thickness direction.

7. The article according to claim 1, wherein said retaining layer is an elastic member comprising thermoplastic synthetic fibers with a basis weight of from about 100 to about 1500 g/m$^2$ and a fineness of from about 6 to about 100 deniers, said fibers being heat-sealed and/or mechanically intertwined together to form said three dimensional network structure, and said retaining layer has a compressivity such that, under a load of about 35 g/cm$^2$, said retaining layer has a thickness T2 of from about 40 to about 80% of a thickness T1 said retaining layer has under a load of about 2 g/cm$^2$.

8. The article according to claim 7, wherein said thermoplastic synthetic fibers contained in said retaining layer are hydrophilic.

9. The article according to claim 1, wherein said retaining layer comprises thermoplastic synthetic fibers of 100 parts by weight and non meltable hydrophilic fibers of 1~100 parts by weight.

10. The article according to claim 1, wherein said retaining layer is further formed with a plurality of channels each having a cross-sectional area of at least 1 mm$^2$ and extending laterally from an opening formed in a inner peripheral surface of said retaining cavity in parallel to said top layer.

11. The article according to claim 2, further comprising an absorbent layer comprising a water absorbent material disposed between said retaining layer and said back layer.

12. The article according to claim 11, wherein said absorbent layer has a basis weight of from about 20 to about 600 g/m$^2$ and an absorptivity of at least 8 g/g for physiological saline.

13. The article according to claim 11, wherein said absorbent layer is exposed at a bottom of said retaining cavity.

14. The article according to claim 11, wherein said absorbent layer has a basis weight of from about 20 to about 600 g/m$^2$ and 40~100 parts by weight of said basis weight are occupied by absorbent fibers.

15. The article according to claim 7, wherein at least 50% by weight of the thermoplastic synthetic fibers contained in said retaining layer are of a fineness of from about 10 to about 70 deniers.

16. The article according to claim 11, wherein said absorbent layer has a thickness of from about 0.1 to about 20 mm.

17. The article according to claim 11, wherein from 0 to about 70% by weight of said absorbent layer is occupied by resin having high water absorptivity.

18. A disposable absorbent article, comprising a hydrophobic topsheet having an opening through which fecal matter can pass, a fecal matter retaining layer, a moisture absorbent layer and a liquid-impervious backsheet successively laminated one with another in this order so that said fecal matter retaining layer and moisture absorbent layer are enclosed between said topsheet and backsheet, wherein:

said topsheet is formed with at least one said opening having an area of from about 20 to about 30000 mm$^2$;

said retaining layer is an elastic member having a thickness of from about 5 to about 100 mm, air/water permeability in a thickness direction and in a planar direction intersecting said thickness direction at substantially the right angle, elastic recovery of at least 50% from a compressed state in said thickness direction; and said retaining layer is provided with at least one fecal matter retaining cavity formed immediately below said opening of said topsheet so as to have substantially the same opening area as said area of said opening and a depth of at least 2.5 mm.

19. A disposable absorbent article having a crotch section corresponding to a crotch region of a wearer and front and rear sections disposed at longitudinally opposite ends of the crotch section, said absorbent article comprising a liquid permeable topsheet, a liquid impermeable backsheet, and a core completely enclosed between and by said topsheet and backsheet; wherein said core comprises a fecal matter retaining layer immediately beneath said topsheet, and a moisture absorbent layer beneath said retaining layer;

said topsheet is formed with at least a through opening in a region that will be placed against a predetermined region of the wearer's hip extending around his/her anus when said article is put on the wearer's body;

said retaining layer is an elastic, compression recoverable member having three dimensional air/water permeability, and said retaining layer is provided with at least a fecal matter retaining cavity formed corresponding to and immediately below said through opening of said topsheet; and said retaining layer is present in all the front, crotch and rear sections of said absorbent article.

20. The article of claim 19, wherein said absorbent core is coexistent with said retaining layer substantially throughout an entire area of said retaining layer.

21. The article of claim 19, wherein an overall thickness of said core is substantially uniform throughout an entire area thereof, except for said retaining cavity.

22. The article of claim 20, wherein a thickness of said absorbent layer is substantially uniform throughout an entire area thereof.

23. The article of claim 19, wherein said retaining cavity extends through an entire thickness of said retaining layer so that said absorbent layer is exposed at a bottom of said retaining cavity.

24. The article of claim 19, wherein said topsheet comprises an upper layer which is hydrophobic and a lower layer which is liquid-pervious, said hydrophobic layer is present at least in the vicinity of a periphery of said opening.

25. The article of claim 24, wherein said hydrophobic layer is not present in edge regions of said core.

26. The article of claim 19, wherein said topsheet is further formed with at least a slit extending through an entire thickness thereof and outwardly from said opening; and said retaining layer is further provided with at least a channel formed corresponding to and immediately below said slit of said topsheet so that fecal matter discharged on top of said channel may directly pass through said slit to be received in said channel.

27. The article of claim 26, wherein said slit and channel communicate at least two said retaining cavities.

28. The article of claim 26, wherein a depth of said channel is less that that of said retaining cavity.

29. The article of claim 19, wherein said absorbent layer extends substantially continuously, seamlessly in all the front, crotch and rear sections of said absorbent article.

* * * * *